United States Patent [19]

Taylor

[11] Patent Number: 5,201,416
[45] Date of Patent: Apr. 13, 1993

[54] HEMOSTATIC CLIP CARTRIDGE

[75] Inventor: Warren Taylor, Cary, N.C.

[73] Assignee: Edward Weck Incorporated, Research Triangle Park, N.C.

[21] Appl. No.: 601,833

[22] Filed: Oct. 22, 1990

[51] Int. Cl.⁵ ............................................ B65D 85/00
[52] U.S. Cl. ................................... 206/339; 206/340; 206/63.3
[58] Field of Search ............... 206/63.3, 338, 339, 206/340, 346, 347, 438; 606/139, 151, 159; 227/175, 176, 177, 901, 902

[56] References Cited

U.S. PATENT DOCUMENTS

| | | | |
|---|---|---|---|
| 3,351,191 | 11/1967 | Mallina | 206/339 |
| 4,076,120 | 2/1978 | Carroll et al. | 206/339 |
| 4,212,390 | 7/1980 | Raczkowski et al. | 206/339 |
| 4,294,355 | 10/1981 | Jewusiak et al. | 206/339 |
| 4,619,262 | 10/1986 | Taylor | 277/177 |
| 4,696,396 | 9/1987 | Samuels | 206/340 |
| 4,961,499 | 10/1990 | Kulp | 206/339 |

FOREIGN PATENT DOCUMENTS

1309342 3/1973 United Kingdom ................ 227/176

*Primary Examiner*—David T. Fidei
*Attorney, Agent, or Firm*—Gene Warzecha

[57] ABSTRACT

A holder for storing and retaining a plurality of hemostatic clips. The holder is produced as an integrally molded unitary piece having a plurality of longitudinally spaced chambers, each having a central post to support a clip and integrally formed guiding means for guiding the jaws of an associated forceps-type clip applier by which a clip within a selected chamber may be removed from the cartridge. A pair of opposing projections are formed in the walls of each clip chamber at a point spaced above the central post, the projections serving to loosely retain a clip in the chamber between the projections and the central post.

6 Claims, 8 Drawing Sheets

HEMOSTATIC CLIP CARTRIDGE

BACKGROUND OF THE INVENTION

1. Field of the Invention

The invention relates generally to holders for storing and retaining hemostatic clips prior to use. More particularly, the invention relates to hemostatic clip cartridges which facilitate the storage and retention of a plurality of hemostatic clips within a corresponding plurality of individual chambers of the cartridge prior to withdrawal of the clips by a forceps-type clip applier.

2. Description of the Prior Art

Hemostatic clips have long been used to ligate or clamp blood vessels during surgical procedures. The clips are generally made of either a biocompatible metallic material or of a polymeric or non-metallic material The term "non-metallic" as used herein means anything other than metallic materials. In general, the clips are generally C-shaped, U-shaped or V-shaped and are designed such that the opposing legs of the open clip are able to be closed together by being compressed by the jaws of a forceps-type clip applier. In the case of metallic clips, the material is sufficiently strong such that the clips remain in their crimped, closed position merely by squeezing the legs together. In the case of plastic-type clips, the material is not as strong and requires some auxiliary latching mechanism to keep the clips closed. For the foregoing reasons, metallic clips are generally symmetrical while plastic clips are not. The latching mechanism generally comprises a hook-type arrangement molded with or otherwise secured to the plastic clip. One example of such a plastic ligating clip is shown in U.S. Pat. No. 4,834,096 (Oh et al.) assigned to the assignee hereof.

Because the clips are small and because many clips are usually used in a surgical procedure, holding devices are used to store and retain the clips—whether metallic or plastic—between the time of their manufacture and ultimate use in a surgical procedure. While numerous clip cartridges are known, they all serve to prevent the clips from becoming loosened during shipment and handling and from becoming completely dislodged. A distinction should be made between clip cartridges intended for use with "manual" clip appliers and those intended for use with "automatic" clip appliers. As used herein, the term "automatic" means those clip appliers which retain a plurality of hemostatic clips adjacent the jaws of a clip applier in a way such that a new clip is automatically fed to the jaws after the previous clip has been crimped into place. As used herein, the term "manual" means clip appliers which receive one clip at a time between the jaws and which have to be reloaded manually after the previous clip is crimped. The reloading operation is generally accomplished by inserting the jaws of the applier into a clip holder or cartridge which is generally provided with a plurality of longitudinally spaced, clip retaining chambers. A single clip is retained in each chamber by a variety of means and removed from its chamber by a forceps-type clip applier which is inserted as desired into each clip chamber and secured to the clip sufficiently to overcome whatever clip retention means is utilized to enable the clip to be removed from the clip chamber.

Various mechanisms are known by which clips may be retained within the chambers of clip cartridges. With respect to metallic clips, friction between the clip and the side walls of its individual chamber is generally sufficient to retain the clip. The clip cartridges are generally made of molded plastic material such that the walls of each clip chamber are somewhat resilient and able to be pushed away from each other when the clip applier jaws are inserted into the chamber to retrieve the clip. An example of a cartridge holding the clips in their respective clip chambers by means of frictional engagement with the side walls of each chamber is shown in U.S. Pat. No. 4,076,120 (Carroll et al.). In some prior art clip cartridges, each individual clip chamber is provided with a central post generally conforming to the shape of the open clip although being slightly larger so that when the clip is pushed onto the central post, frictional contact between the legs of the clip and the central post retains the clip within its chamber. Cartridges of this type are shown in U.S. Pat. Nos. 3,270,745, 3,326,216, 3,363,628, 3,439,522 and 3,439,523, all issued to E. C. Wood.

Prior art cartridges are also known which retain clips in a partially straightened state by maintaining each clip under tension within its chamber by the interaction between the central post in the chamber and the central part of the clip and protrusions extending into each chamber toward the central post (from the ends). The clip is retained by having its central hinge part pushed upwardly by the central post and its ends pushed downwardly by the protrusions. Such a cartridge is shown in U.S. Pat. No. 3,713,533 (Reimels) and U.S. Pat. No. 4,146,130 (Samuels et al.)

Another type of prior art cartridge is known which has a plurality of ribs extending from each side wall of each clip chamber inwardly toward the clip to retain the clip by frictional engagement with the ribs (U.S. Pat. No. 4,696,396, Samuels). The aforementioned U.S. Pat. No. 4,146,130 (Samuels et al.) shows an alternative embodiment for the situation where clips are intended to be loosely maintained in the cartridge without frictional engagement between it and the chamber, the clips in such an event being retained in each cartridge by a covering tape which may be easily severed by the applier as desired.

With respect to non-metallic clips, the prior art cartridges suitable for holding metallic clips are not necessarily suitable because the plastic clips inherently have a greater resiliency and non-symmetrical structure. For example, the aforementioned prior art cartridges which rely on the interaction between the clip and central post are not suitable for use with non-metallic clips because there is generally insufficient compression in non-metallic clips to cause them to grip the center post adequately. Likewise, frictional engagement with either the side and/or end walls of the chamber could possibly, over a long period of storage time, adversely affect performance of the clips. It would be preferable to retain non-metallic clips in a natural, relaxed state without any external stress applied to the clips until they are ready for use.

One known prior art method of holding plastic clips is shown in U.S. Pat. No. 4,294,355 (Jewusiak et al.) which discloses one or more resilient fingers associated with each clip chamber for holding each clip in a particular fixed orientation. The entire cartridge may or may not be covered by a thin film having a plurality of lines of weakness over each clip to identify the clip location for easy retrieval by the clip applier.

U.S. Pat. No. 4,361,229 (Mericle) discloses a cartridge for non-metallic clips wherein each clip is retained in its individual chamber by the interaction between a central post supporting each clip and paper flaps extending into each end of each chamber, the paper flaps being formed from a paper film interposed between a base portion of the cartridge (to which the central post is secured) and a top portion.

The known prior art cartridges suitable for non-metallic clips are relatively complex to manufacture and load and it is an object of this invention to produce a hemostatic clip holder of simplified structure and which also simplifies the loading of clips into the holder.

It is another object of this invention to provide a hemostatic clip holder for retaining clips during shipping and handling while enabling the withdrawal of the clips by clip appliers in preparation for use.

It is also an object of this invention to produce a unitary clip holder for storing and retaining a plurality of hemostatic clips for subsequent removal by an associated clip applier.

It is a further object of this invention to produce a hemostatic clip holder for storing and retaining a non-metallic hemostatic clip for subsequent removal by an associated clip applier.

It is a further object of this invention to produce a hemostatic clip cartridge for storing and retaining a plurality of non-metallic hemostatic clips in a natural, relaxed state prior to their subsequent removal by an associated clip applier.

SUMMARY OF THE INVENTION

These and other objects of this invention are achieved by the preferred embodiment of the invention disclosed herein which is embodied in a cartridge for holding hemostatic clips comprising an elongated body forming a plurality of longitudinally spaced chambers, each chamber for receiving a hemostatic clip. Each chamber has a central post for supporting an open hemostatic clip and a pair of facing transverse walls extending across the body, each of the transverse walls having a pair of recessed wall surfaces on each side of the central post, the transverse walls and the recessed walls being joined by longitudinally extending ledge surfaces. A projection extends into each chamber from each transverse wall at a point spaced above the central post, thereby forming a pair of opposed projections to retain a clip in the chamber below the projections.

DESCRIPTION OF THE PREFERRED EMBODIMENT

Figure 1:
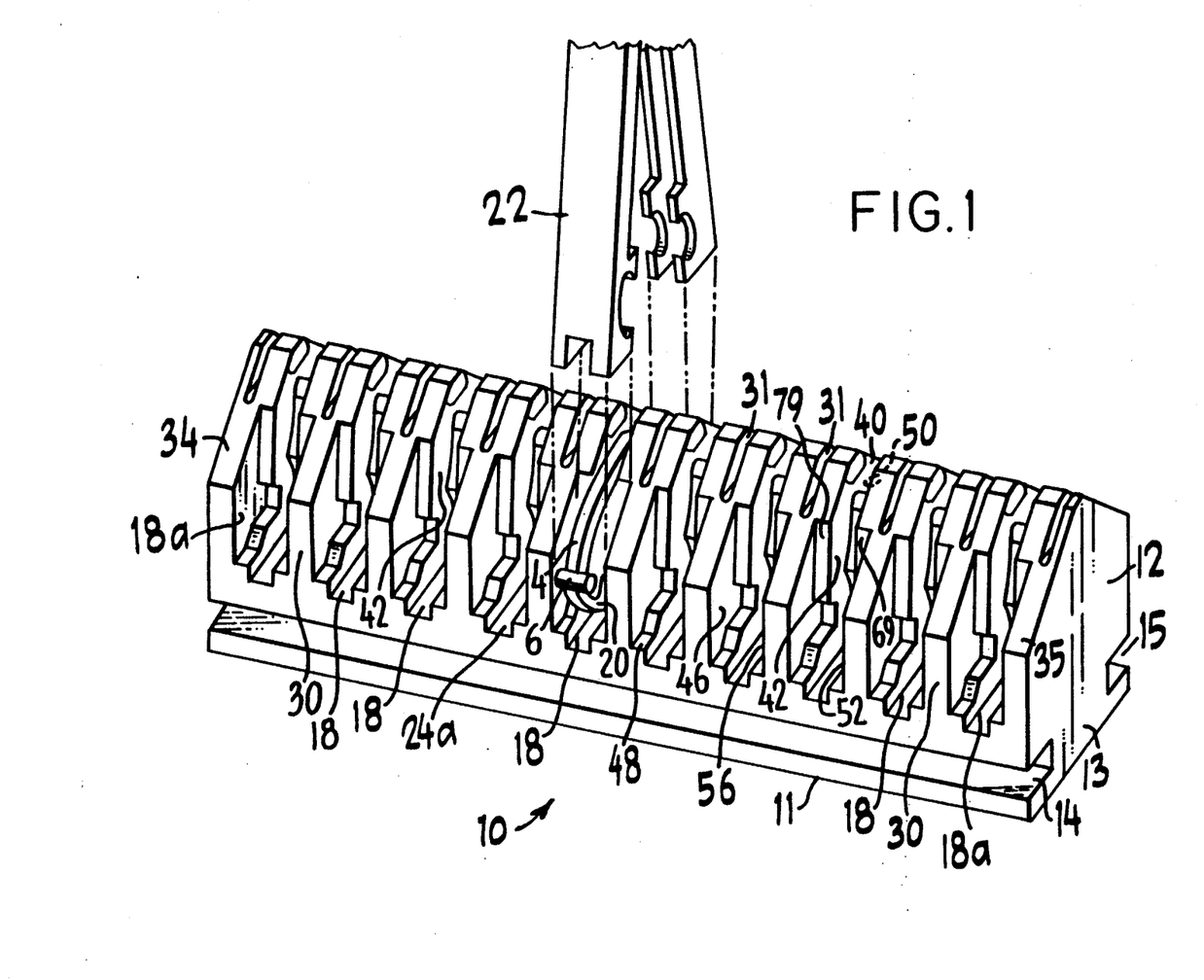
FIG. 1 is a perspective view of a hemostatic clip cartridge constructed in accordance with the principles of this invention, the cartridge shown with a single hemostatic clip and an associated portion of a clip applier in position above the clip.

Referring now to FIG. 1, there is shown a preferred embodiment of the clip cartridge 10 constructed in accordance with the principles of this invention.

Clip cartridge 10 is a single molded plastic component comprising a plurality of longitudinally spaced, individual clip retaining chambers 18, each of which is identical and retains a clip 20 (only one of which is shown). Clip 20 is a non-symmetrical hemostatic clip of the type shown in U.S. Pat. No. 4,834,096 (Oh et al.), assigned to the assignee hereof and incorporated by reference herein. As best seen in FIGS. 1 and 10-13 and in the aforementioned '096 patent, clip 20 comprises an integral plastic C-shaped body 4 with two legs hinged at a central point and a pair of lateral engagement means or bosses 6 and 8 near the ends of the legs. As will be understood below, bosses 6 and 8 interact with portions of cartridge 10.

Cartridge 10 has a base portion 11, a body portion 12 and a neck portion 13 interposed between the body and base in order to define channels 14 and 15 which serve to facilitate securing the cartridge to a tray or other component during use. It will be noted that cartridge 10 is symmetrical about its longitudinal centerline and this facilitates its manufacture as well as its assembly with clips 20. The jaw portion of a representative clip applier 22 is diagrammatically shown in position over clip 20 in one of the clip chambers 18.

Figure 4:
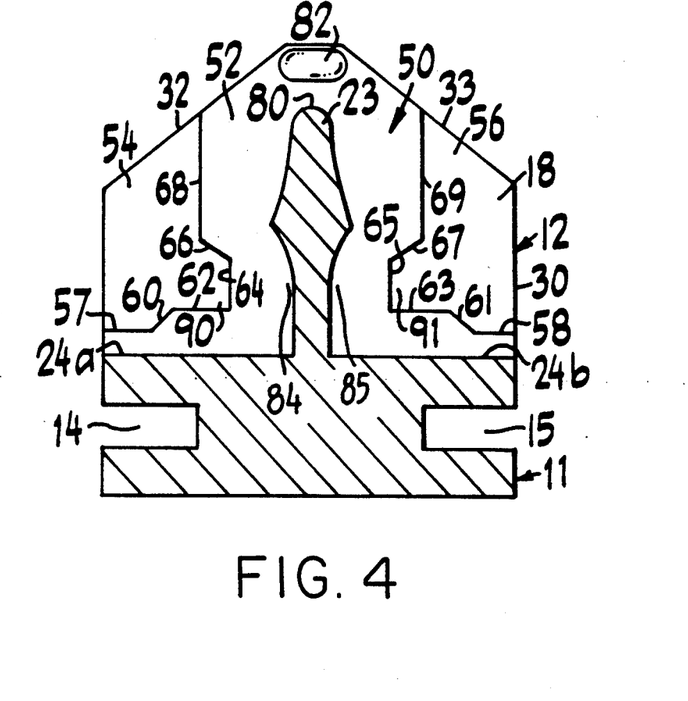
FIG. 4 is a cross-sectional view of FIG. 2 taken along the lines 4—4.

As best seen in FIGS. 1-4, adjacent clip chambers 18 are separated by transverse walls 30 which (at their bases) extend across the width of body 12 (best seen in FIG. 4). The end clip chambers 18a obviously have a wall 30 only on one side and are bounded on the opposite side by end wall portions 34 and 35 of body 12, as the case may be. These end wall portions have some similarity to walls 30 in order to insure that end chambers 18a are identical in operation to intermediate chamber 18. Each wall 30 and end walls 34 and 35 have a transverse slit 31 near their upper ends, the purpose of which will be discussed below. The upper surface of each wall 30 is tapered at 32 and 33 to reduce cartridge mass and improve the accessibility of the clips.

Figure 2:
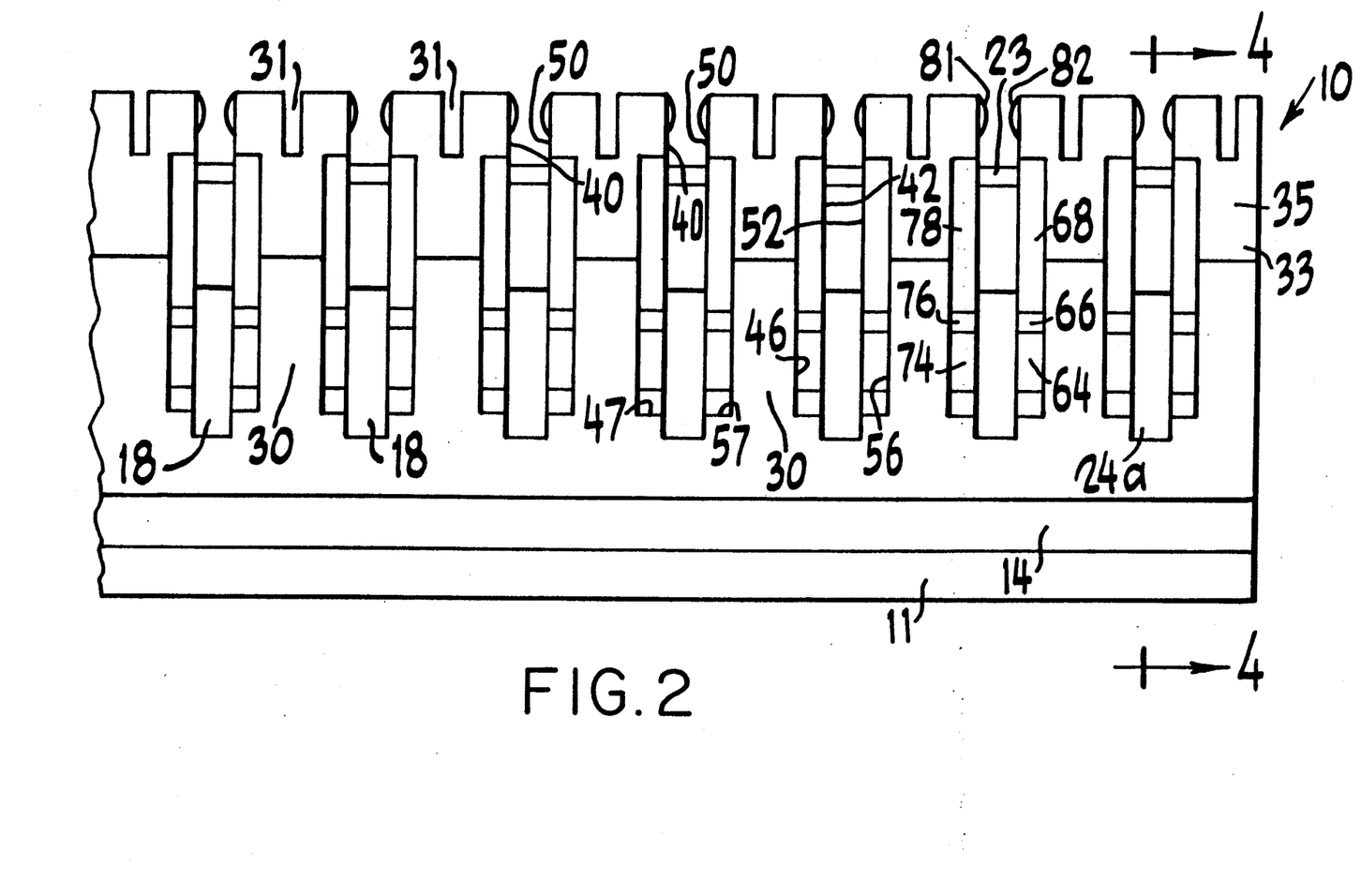
FIG. 2 is a side elevational view of the clip cartridge of FIG. 1.
Figure 3:
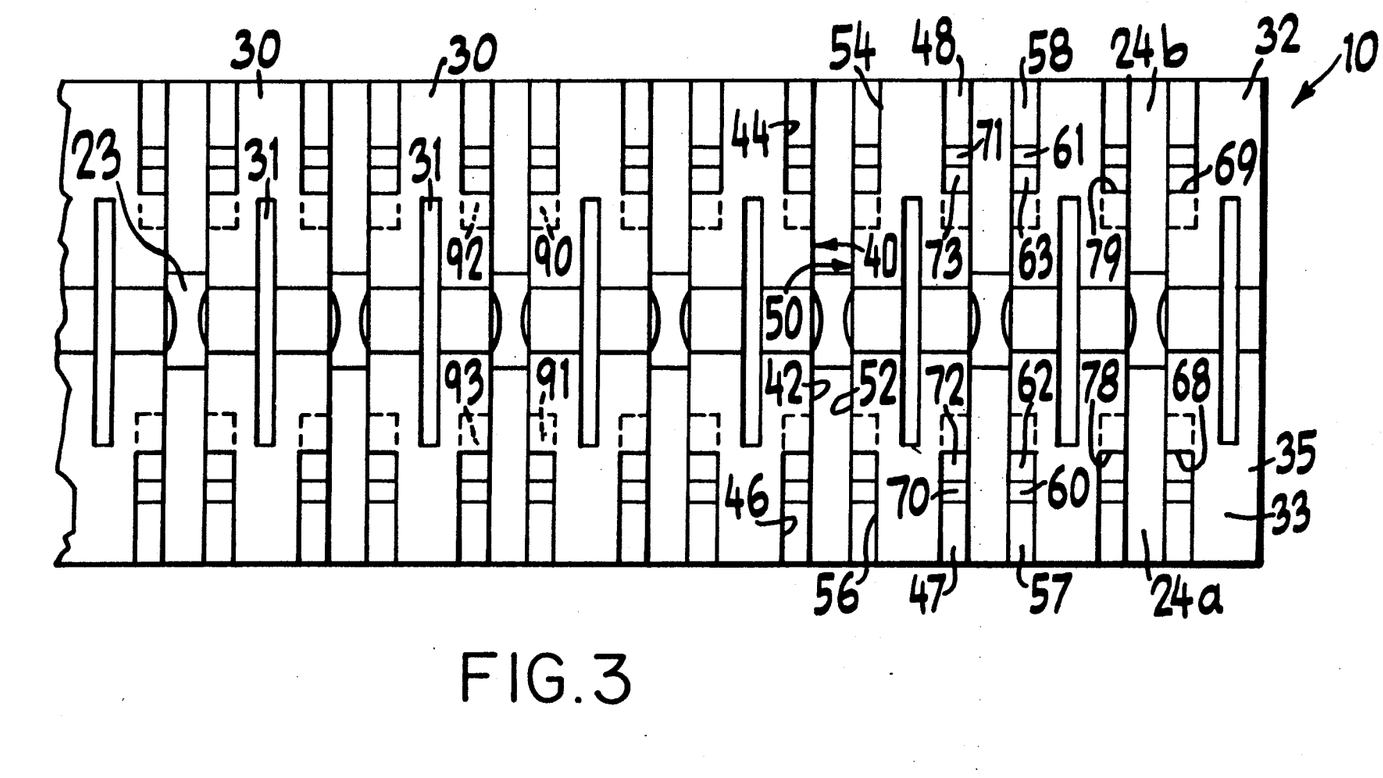
FIG. 3 is a top plan view of FIG. 2.

Each wall 30 has a pair of symmetrical and oppositely facing transverse walls 40 and 50 which form the sides of each chamber 18: surface 40 facing inwardly into clip chamber 18 from one wall 30 and surface 50 facing inwardly into the same clip chamber 18 from an adjacent wall 30. For simplicity, the walls facing to the right in FIG. 2 are each identified as 40 and those facing to the left are each identified as 50. Each clip chamber 18 is also provided with an integral central post 23, interposed between facing walls 40 and 50, and has floor portions 24a and 24b on either side of the post. Walls 40 and 50 are formed by a variety of facing symmetrical and parallel wall and ledge surfaces, best seen in FIGS. 2, 3 and 4 and described below. In view of the symmetrical nature of cartridge 10 and facing wall surfaces 40 and 50, for simplicity only the features of one clip chamber 18 will be described in detail.

Wall 50 is shown in detail in FIG. 4, but it will be understood that the features of wall 50 have symmetrical counterparts on wall 40. Wall 50 includes a main portion 52 which is spaced from its symmetrical facing surface 42 by an amount slightly greater than the width of the body 4 of clip 20 to be received in chamber 18. Wall 50 has recessed wall portions 54 and 56 symmetrically arranged on either side of main portion 52, and wall 40 has facing recessed wall portions 44 and 46. The distance between facing surfaces 44/54 and 46/56 is greater than the spacing between facing main portions 42 and 52. The difference in these spacings accommodates lateral bosses 6 and 8, creating longitudinally extending ledges perpendicular to wall portions 54, 56 and 44, 46, the purpose of which will be discussed below, and provides access to the jaws of clip applier 22 while limiting any twisting of clips 20 in their chambers.

Surfaces 40 and 50 may have any variety of selected profiles; however, in a preferred embodiment the recesses 54, 56 and 44, 46 do not extend entirely across the width of body 12 or to the bottom of channel 18, thereby forming bottom ledges 57, 58 and 46, 48 parallel to and on either side of the floor 24a/24b of each chamber 18. The inner ends of ledges 57, 58 and 47, 48 are each angled inwardly and upwardly to form inclined ramps 60, 61, 70 and 71, respectively, which merge into flat ledges 62, 63 and 72, 73, respectively. The profile of recesses 54, 56 and 44, 46 continues upwardly from the inner edges of ledges 62, 63 and 72, 73 to form vertical ledges 64, 65 and 74, 75 at the upper ends of which recesses 54, 56 extend diagonally upwardly and outwardly to form ledges 66, 67 and 76, 77 and then upwardly to form ledges 68, 69 and 78, 79 to the top of body 12. The ledges 62, 64, 66 and 63, 65, 67 form recesses 90 and 91 which, as will be seen in FIGS. 10a and 10b, receive lateral boss 6 to allow clip 20 to balance itself on post 23. (Wall 40 has a symmetrical pair of recesses 92 and 93.)

Figure 5:
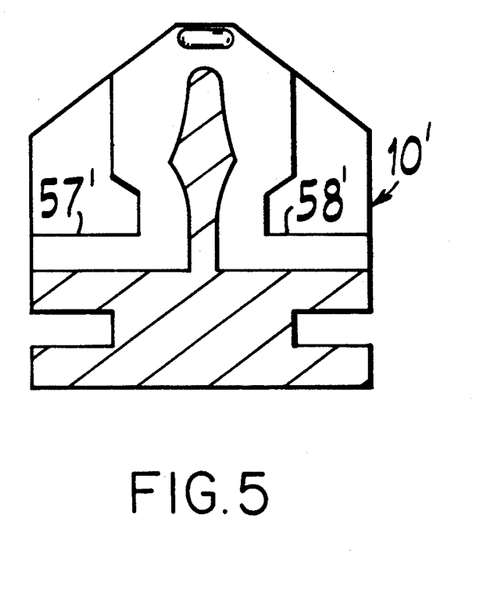
FIG. 5 is an alternative embodiment of FIG. 4.
Figure 6:
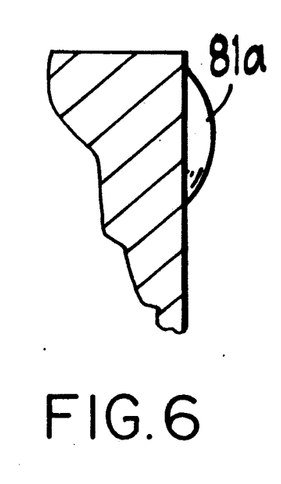
FIGS. 6, 7, 8 and 9 are diagrammatic side elevation views of alternative embodiments of a portion of the invention
Figure 6A:
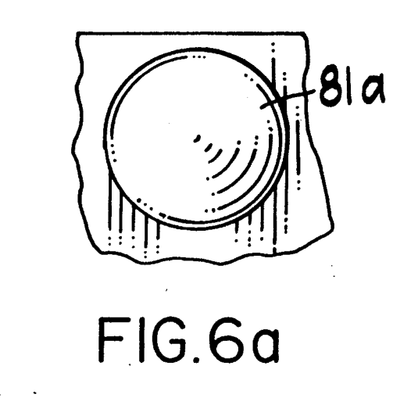
FIGS. 6a, 7a, 8a and 9a are corresponding front elevation views of portions thereof.
Figure 7:
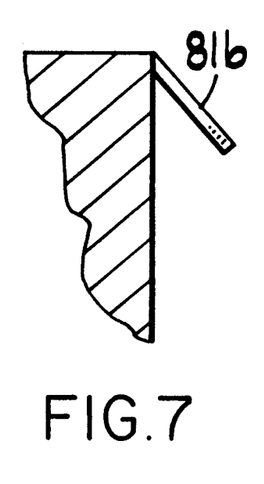
Figure 7A:
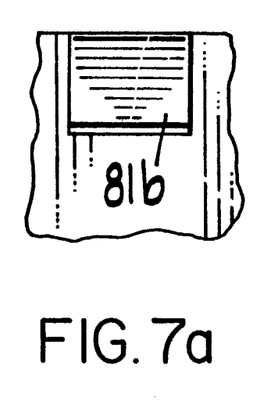
Figure 8:
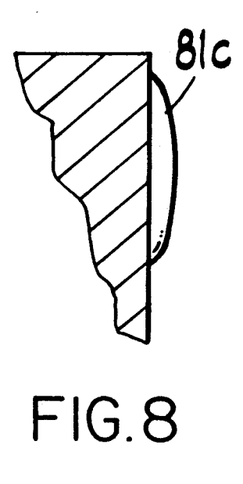
Figure 8A:
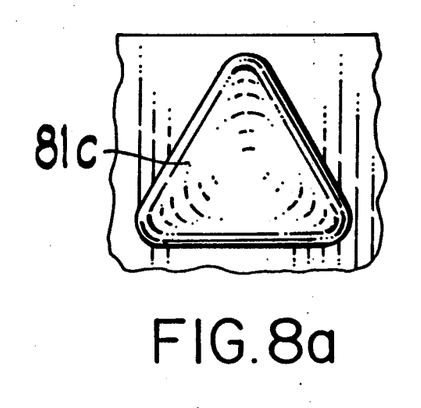
Figure 9:
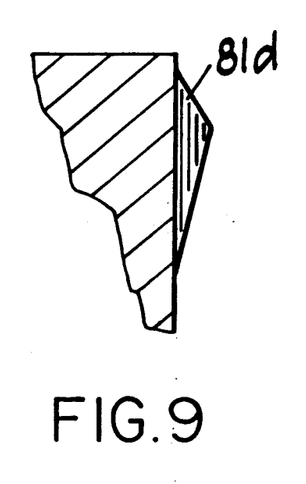
Figure 9A:
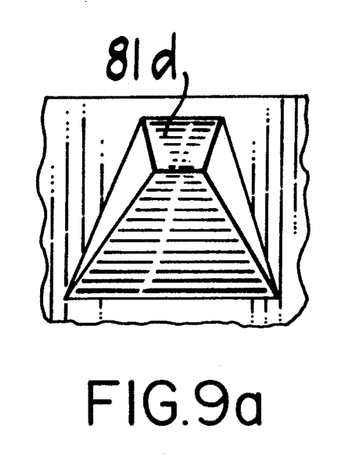
Figures 14, 19, 20:
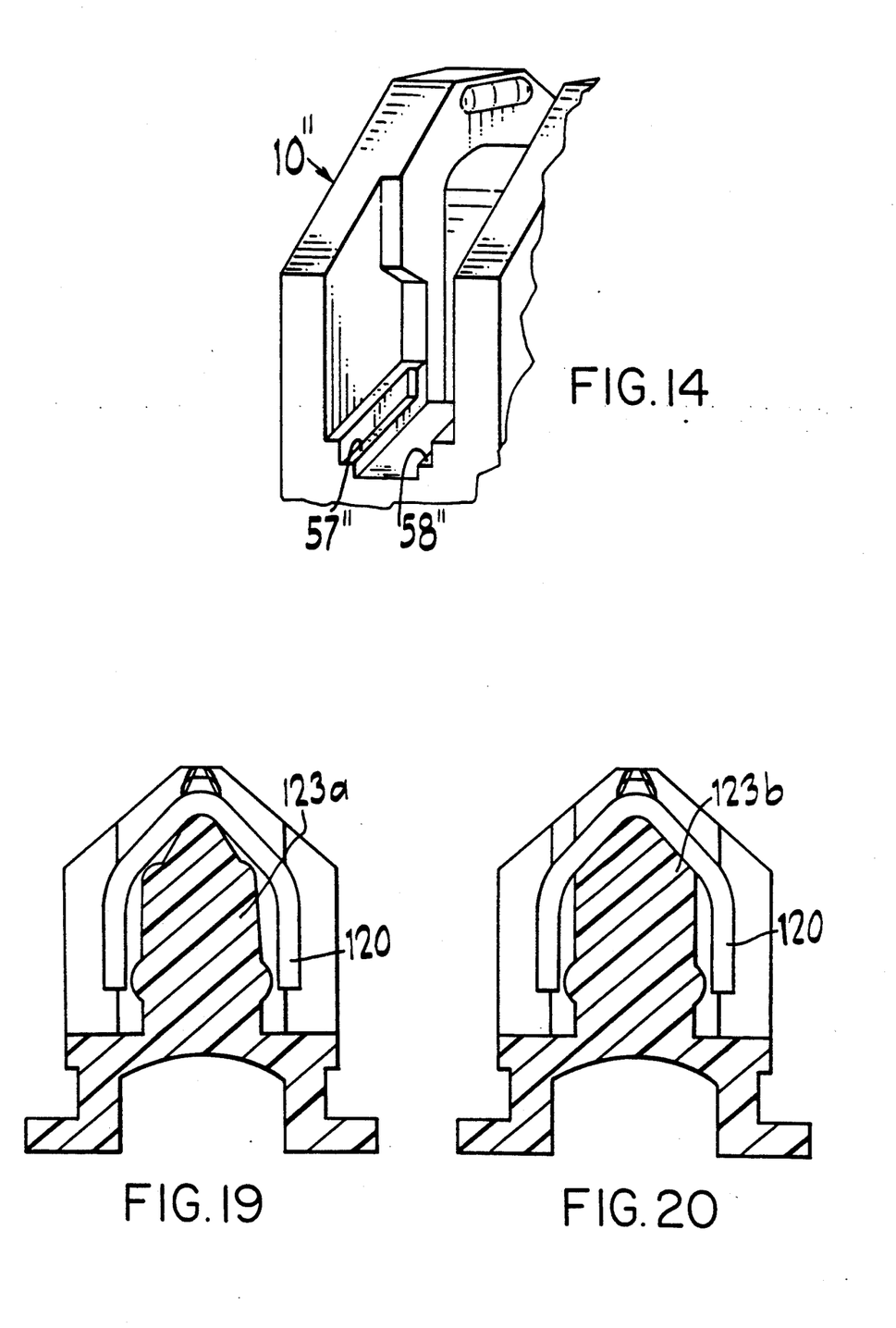
FIG. 14 is a diagrammatic view of an alternate embodiment of a portion of the clip chamber shown in FIG. 1.
FIGS. 19 and 20 are alternate view of FIG. 17 showing differently shaped central posts.

As shown in FIG. 5, an alternate embodiment 10' may be made in which bottom ledges 57, 60, 62 and 58, 61, 63 are replaced by straight ledges 57' and 58', respectively, all other parts of cartridge 10' being identical to cartridge 10. Those skilled in the art will understand that the various ledges in each clip chamber 18 may be shaped differently to accommodate different clip structures and to conform to various shapes of clip applier tips. Furthermore, as shown in FIG. 14, an alternate embodiment 10" may be made in which ledges 57' and 58' may also be modified to produce facing steps 57" and 58" to provide clearance for projecting sharp distal points of clip 20 as it is compressed by the applier jaws.

Figures 11, 12, 13:
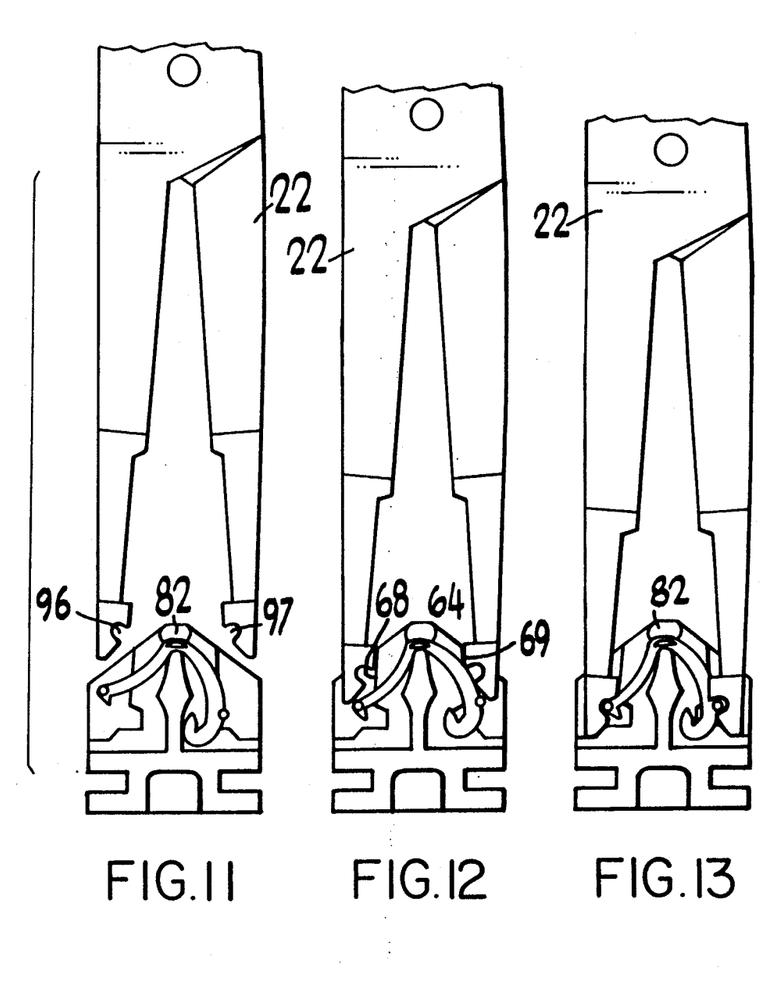
FIGS. 11, 12 and 13 show the sequence of steps by which a polymer clip retained within a clip compartment of the cartridge of FIG. 1 may be withdrawn by a clip applier.

Ledge pairs 68/78 and 69/79 on either side of center post 23 serve as guides to center a clip applier as it enters chamber 18 to ensure proper insertion of the clip into the applier jaws as will be better seen in FIGS. 11-13. The bottommost ledges in the various embodiments (e.g. 57, 58, 57', 58') primarily serve as a stop for the downward movement of the applier into the cartridge. Ledges 60, 61 and 70, 71 also serve to center the particular jaw tips shown in FIGS. 11-13.

Figure 10A:
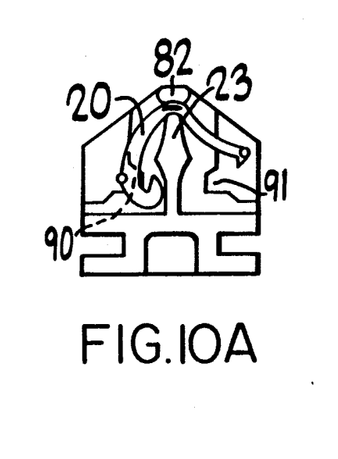
FIGS. 10a and 10b are diagrammatic views of a single clip compartment of the clip cartridge of FIG. 1 shown with a polymer clip in various orientations.
Figure 10B:
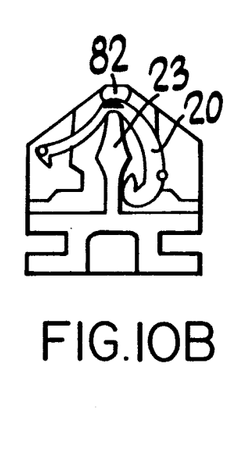

Spaced above the upper tip 80 of central post 23 are inwardly directed, facing and symmetrical protrusions 81 and 82 integrally formed near the apices of surfaces 40 and 50, respectively. Protrusions 81 and 82 serve as clip retaining means by slightly narrowing the distance between faces 40 and 50 in part of the area above central post 23. As shown in FIGS. 6, 7, 8 and 9, protrusions 81, 82 may be formed in a variety of shapes, 81a, 81b, 81c and 81d, all integrally molded with surfaces 40 and 50. Central post 23 is provided with a pair of opposed recesses 84 and 85 to accommodate the hook end of clip 20 to enable the clip to balance itself on the post (as best seen in FIGS. 10a and 10b). The structure of cartridge 10 facilitates its use with non-symmetrical polymeric hemostatic clips 20 of the type shown in the aforementioned U.S. Pat. No. 4,834,096. Obviously, cartridge 10 would also be suitable for symmetrical metallic or non-metallic clips. The provision of a narrow central post 23 and a pair of retaining means 81 and 82 spaced above the post so as not to directly press inwardly on the body of clip 20 enables the clip to rock somewhat about the tip of central post 23 thereby facilitating its subsequent retrieval by clip applier 22 as best seen in FIGS. 11, 12 and 13. It will be noted that the recesses on either side of post 23 accommodate the hook end of clip 20 regardless of whether the hook is on the left (FIG. 10a) or right (FIG. 10b). The recesses 90, 91 serve to receive the lateral bosses of the particular clip shown in the aforementioned patent. This symmetry facilitates loading clips into the cartridge because particular attention need not be paid to whether the clips are facing right or left.

The retrieval of clips 20 from clip chambers 18 by clip applier 22 is best seen by referring to the sequence of events depicted in FIGS. 11, 12 and 13. It will be understood that these drawings only show one side of chamber 18. As shown in FIG. 11, prior to the insertion of clip applier 22 into clip chamber 18, clip 20 may be balanced about post 23 in a variety of random orientations only one of which is depicted in FIG. 11. Nevertheless, regardless of clip orientation, as clip applier 22 is inserted into chamber 18 and comes into contact with vertical guiding ledges 68, 69 the applier jaws will be guided to cause them to properly contact boss 8 of clip 20 (shown in FIG. 12) and pivot the clip accordingly. It is noted that the invention thus has an automatic self-alignment feature in that clip 20 will be forced to pivot about the tip of center post 23 thereby insuring that the lateral latching means on each leg of the clip will be properly aligned and placed adjacent to the corresponding recesses 96, 97 on the clip jaws. When the clip applier is further inserted into the chamber as shown in FIG. 13, the interaction between the lateral bosses on each leg of the clip and the recesses on each jaw of the clip applier causes the clip to be compressed slightly and causes the lateral bosses on the clip to become seated in the recesses of the jaws of the applier. It will be understood that slight upward movement of the applier from the position shown in FIG. 13 will cause clip 22 to ride over protrusions 81 and 82, the deflection of which is facilitated by slit 31, thereby removing the clip from its chamber.

Referring now to FIGS. 15 through 20, there is shown an alternate embodiment of the invention in the form of clip cartridge 100 having a plurality of longitudinally spaced clip chambers 118 for retaining hemostatic clips 120. As previously mentioned, the invention is suitable for use with metallic and non-metallic hemostatic clips and cartridge 120 is described in conjunction with metallic hemostatic clip 120 which may or may not be coated with hydroxyapatite or some other grasping enhancing material. Cartridge 100 is suitable for ??In the situation where coated metallic clips are utilized and it is desired to provide a clip cartridge which retains the clip in a manner which significantly reduces any likelihood of scratching or otherwise maring the coating.

Figure 15:
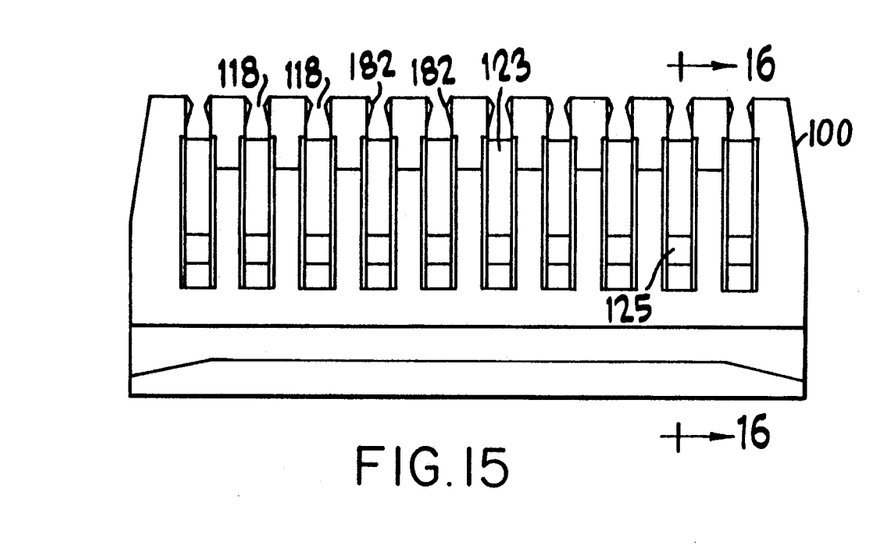
FIG. 15 is a diagrammatic side elevational view of an alternative embodiment of the hemostatic clip cartridge of FIG. 1.
Figure 16:
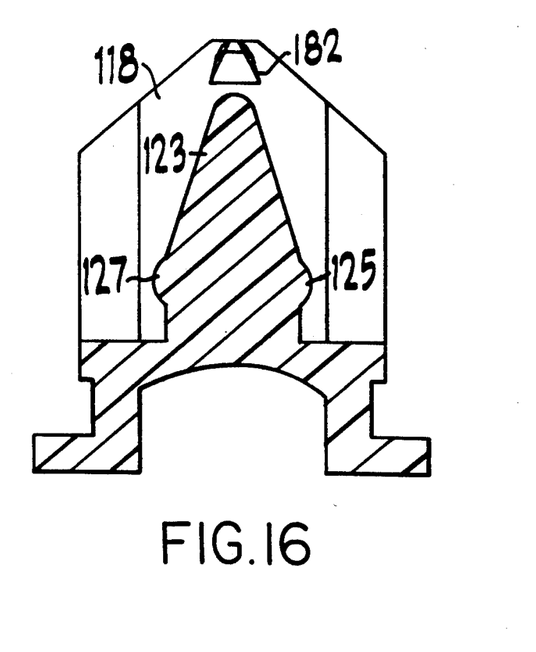
FIG. 16 is a cross-sectional view of FIG. 15 taken along the line 16—16.
Figure 17:
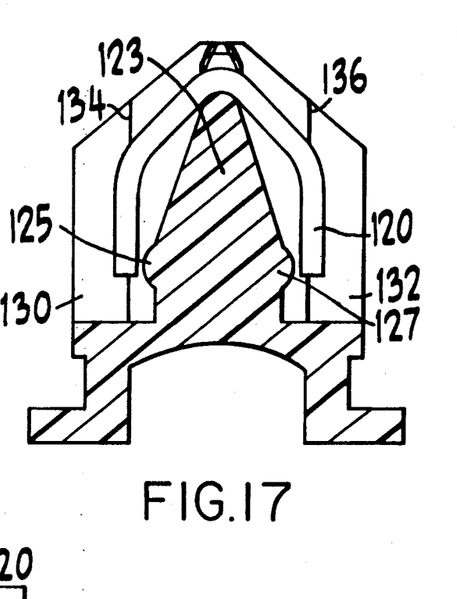
FIG. 17 is a view of FIG. 16 including a hemostatic clip.

Each chamber 118 has opposed and inwardly extending projections 182, best seen in FIGS. 15 and 16 protrusions 182 operate in conjunction with center post 123 in the same manner as the previously described embodiments. In cartridge 100, however, center post 123 has a pair of opposed and outwardly extending projections 125, 127 situated adjacent the base of each center post 123, the projections intended to lie adjacent the ends of the legs of clip 120 (as best seen in FIG. 17) to assist in stabilizing the clip. As seen in FIGS. 19 and 20, center post 123 may be provided in alternative embodiments 123A and 123B in order to provide different degrees of support and stability for clip 120.

Figure 18:
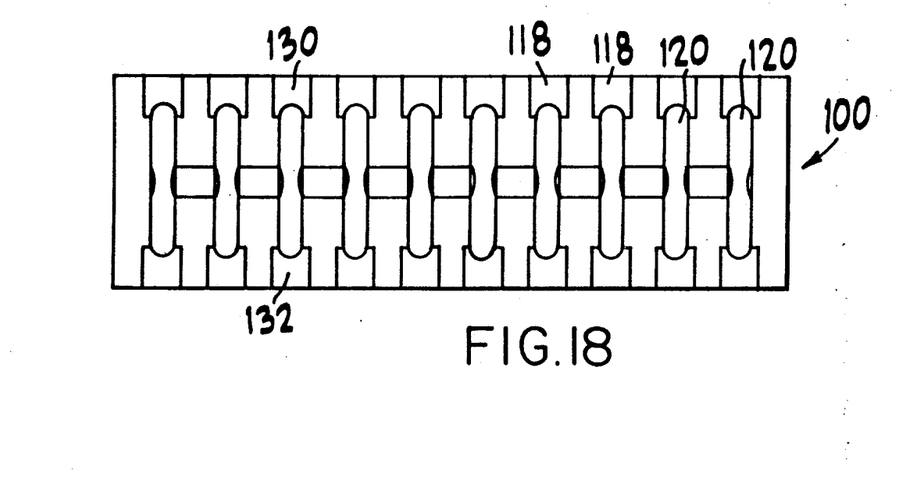
FIG. 18 is a top plan view of the embodiment of FIG. 15 wherein the clip chambers are each filled with a single hemostatic clip.

As best seen in FIGS. 17 and 18, each clip chamber 118 is provided with a pair of forceps receiving channels 130 and 132 for receiving the jaws of an associated forceps-type clip applier which may be inserted into each clip chamber 118 to retrieve the clip situated therein.

As will be understood by those skilled in the art, the longitudinally extending vertical ledges 134 and 136 help to align the clip applier as it is inserted into clip chamber 118 so that the applier may properly engage clip 120.

It will be understood by those skilled in the art that numerous modifications and improvements may be made to the preferred embodiment of the invention disclosed herein without departing from the spirit and scope thereof.

What is claimed is:

1. A cartridge for retaining hemostatic clips comprising:
    a body portion having a plurality of clip retaining compartments longitudinally spaced along said body portion, each compartment formed by a pair of upwardly extending walls, each said compartment having a central post for supporting the hinge portion of a clip and provided, adjacent the distal end of said walls, with a pair of opposed, inwardly extending protrusions, one protrusion extending inwardly from each wall, each pair of said protrusions adapted to extend into the associated compartment above a clip situated within the compartment, each of said protrusions having a bottom edge which terminates on a respective transverse wall at a predetermined distance from the top of said post such that said protrusions are spaced from said clip when said clip rests on said post, said protrusions adapted to be deflected by the clip as it is removed from said compartment.

2. A clip cartridge in accordance with claim 1 wherein the adjacent, upwardly extending walls forming the adjacent compartments are integrally joined together.

3. A clip cartridge in accordance with claim 1 wherein said body portion is integrally molded with said walls and protrusions.

4. A cartridge in accordance with claim 3 further comprising a base portion integrally formed with said body and spaced therefrom to form a pair of parallel, longitudinally extending channels for securing said cartridge to a complimentarily shaped frame means.

5. A holder for holding a hemostatic clip comprising:
    a body portion having a clip retaining compartment formed by a pair of upwardly extending walls, said compartment having a central post for supporting the hinge portion of a clip and provided, adjacent the distal end of said wall, with a pair of opposed, inwardly extending protrusions, one protrusion extending inwardly from each wall, each pair of said protrusions adapted to extend into said compartment above a clip situated therein, each of said protrusions having a bottom edge which terminates on a respective transverse wall at a predetermined distance from the top of said post such that said protrusions are spaced from said clip when said clip rests on said post, said protrusions adapted to be deflected by the clip as it is removed from said compartment.

6. A cartridge for holding hemostatic clips comprising:
    an elongated body forming a plurality of longitudinally spaced chambers, each chamber for receiving a hemostatic clip and comprising:
    a central post for supporting an open hemostatic clip;
    a pair of facing, symmetrical transverse walls having transverse wall surface extending across said body, each of said transverse wall surfaces having a pair of recessed wall surfaces on each side of said post, said transverse wall surfaces and said recessed wall surfaces joined by longitudinally extending ledge surfaces, said ledge surfaces comprising a pair of substantially vertical ledges on either side of said post for guiding the jaws of an associated clip applied into engagement with a clip, each of said transverse walls further comprising an inwardly extending protrusion thereby forming a pair of facing protrusions extending into the associated compartment at a predetermined distance above a clip situated within the compartment, each of said protrusions having a bottom edge which terminates on a respective transverse wall at a predetermined distance from the top of said post such that said protrusions are spaced from said clip when said clip rests on said post, said protrusions adapted to be deflected by the clip as it is removed from the compartment.

* * * * *